(12) United States Patent
Zamft et al.

(10) Patent No.: US 12,254,958 B2
(45) Date of Patent: Mar. 18, 2025

(54) METHODS AND COMPOSITIONS FOR GOVERNING PHENOTYPIC OUTCOMES IN PLANTS

(71) Applicant: HERITABLE AGRICULTURE INC., Mountain View, CA (US)

(72) Inventors: Bradley Michael Zamft, Mountain View, CA (US); Logan Graham, Mountain View, CA (US)

(73) Assignee: HERITABLE AGRICULTURE INC., Mountain View, CA (US)

( * ) Notice: Subject to any disclaimer, the term of this patent is extended or adjusted under 35 U.S.C. 154(b) by 0 days.

(21) Appl. No.: 18/412,306

(22) Filed: Jan. 12, 2024

(65) Prior Publication Data
US 2024/0221865 A1   Jul. 4, 2024

Related U.S. Application Data

(62) Division of application No. 16/870,838, filed on May 8, 2020, now Pat. No. 11,908,547.
(Continued)

(51) Int. Cl.
*G06F 17/00*   (2019.01)
*G06N 5/04*   (2023.01)
(Continued)

(52) U.S. Cl.
CPC .............. *G16B 20/00* (2019.02); *G06N 5/04* (2013.01); *G06N 20/00* (2019.01); *G16B 40/00* (2019.02); *G06Q 50/02* (2013.01)

(58) Field of Classification Search
CPC ........ G16B 20/00; G16B 20/50; G16B 40/00; G06N 5/04; G06N 20/00; G06N 3/045; G06N 3/047; G06N 7/01; G06Q 50/02
See application file for complete search history.

(56) References Cited

U.S. PATENT DOCUMENTS 8,032,389 B2 * 10/2011 Avey .................. G06Q 30/00
  705/1.1
9,465,911 B2 * 10/2016 Hazebroek ............. G16B 20/20
(Continued)

OTHER PUBLICATIONS

Dan He, Irina Rish, David Haws, and Laxmi Parida. 2016. MINT: mutual information based transductive feature selection for genetic trait prediction. IEEE/ACM Trans. Comput. Biol, Bioinformatics 13, 3 , 578-583. <https://doi.org/10.1109/TCBB.2015.2448071>, May (Year: 2016).
(Continued)

*Primary Examiner* — Greta L Robinson
(74) *Attorney, Agent, or Firm* — Kilpatrick Townsend & Stockton LLP

(57) ABSTRACT

Methods, systems, and apparatus, including computer programs encoded on computer storage media, for governing phenotypic outcomes in plants. One method includes obtaining a model input comprising time series data, wherein the time series data comprises, for each previous time point of one or more previous time points, at least one of i) first multi-omics data corresponding to a plant at the previous time point, or ii) phenotypic data corresponding to the plant at the previous time point; and processing the model input using a machine learning model to obtain a model output that comprises, for each future time point of one or more future time points, a prediction of at least one of i) a phenotype of the plant at the future time point, or ii) second multi-omics data corresponding to the plant at the future time point.

20 Claims, 7 Drawing Sheets

Related U.S. Application Data

(60) Provisional application No. 62/845,276, filed on May 8, 2019.

(51) Int. Cl.
  *G06N 20/00* (2019.01)
  *G16B 20/00* (2019.01)
  *G16B 40/00* (2019.01)
  *G06Q 50/02* (2012.01)

(56) References Cited

U.S. PATENT DOCUMENTS

| | | | |
|---|---|---|---|
| 11,195,109 B2* | 12/2021 | Mewes | G06N 20/00 |
| 11,908,547 B2* | 2/2024 | Zamft | G16B 20/00 |
| 2010/0145624 A1 | 6/2010 | Kishore et al. | |
| 2014/0220568 A1 | 8/2014 | Inze et al. | |
| 2019/0050948 A1 | 2/2019 | Perry et al. | |

OTHER PUBLICATIONS

Harfouche et al., "Accelerating Climate Resilient Plant Breeding by Applying Next-Generation Artificial Intelligence," Trends in Biotechnology, Jun. 2019, 37(11):1217-1235.

He et al., "Evaluation of Genomic Prediction for Pasmo Resistance in Flax," Int. J. Mol. Sci., Jan. 2019, 20(2):359.

International Preliminary Report on Patentability in International Appln. PCT/US2020/032253, dated Nov. 18, 2021, 16 pages.

International Search Report and Written Opinion in International Appln. PCT/US2020/032253, dated Sep. 14, 2020, 25 pages.

Invitation to Pay Additional Fees in International Appln. PCT/US2020/032253, dated Jul. 24, 2020, 20 pages.

Jin et al., "Auto-Keras: An Efficient Neural Architecture Search System," In Proceedings of the 25th ACM SIGKDD International Conference on Knowledge Discovery & Data Mining, 2019, pp. 1946-1956.

Kang et al., "Identifying stress-related genes and predicting stress types in *Arabidopsis* using logical correlation layer and CMCL loss through time-series data," 2018 IEEE International Conference on Bioinformatics and Biomedicine, Dec. 3-6, 2018, pp. 399-404.

Kawakatsu et al., "Epigenomic Diversity in a Global Collection of *Arabidopsis thaliana* Accessions," Cell, 2016, 166(2):492-505.

Michel et al., "Genomic selection across multiple breeding cycles in applied bread wheat breeding," Theor Appl Genet., Jan. 2016, 129(6):1179-1189.

Sarinelli et al., "Training population selection and use of fixed effects to optimize genomic predictions in a historical USA winter wheat panel," Theor Appl Genet, Jan. 2019, 132(4):1247-1261.

Tardieu et al., "Plant Phenomics, From Sensors to Knowledge," Current Biology, Aug. 2017, 27(15):R770-R783.

* cited by examiner

METHODS AND COMPOSITIONS FOR GOVERNING PHENOTYPIC OUTCOMES IN PLANTS

CROSS REFERENCE TO RELATED APPLICATIONS

This application is a divisional of U.S. application Ser. No. 16/870,838, filed on May 8, 2020, now allowed, which claims priority under 35 U.S.C. § 119 to U.S. Provisional Patent Application Ser. No. 62/845,276, filed May 8, 2019. The disclosure of the prior applications are considered part of and are incorporated by reference in the disclosure of this application.

BACKGROUND

This specification relates to applications of neural networks, and more particularly to techniques of applying machine learning models to plant biotechnology.

Machine learning models receive an input and generate an output, e.g., a predicted output, based on the received input. Some machine learning models are parametric models and generate the output based on the received input and on values of the parameters of the model.

One type of machine learning model is a neural network. Neural networks, or for brevity, networks, are machine learning models that employ multiple layers of operations to predict one or more outputs from one or more inputs. Neural networks typically include one or more hidden layers situated between an input layer and an output layer. The output of each layer is used as input to another layer in the network, e.g., the next hidden layer or the output layer.

Each layer of a neural network specifies one or more transformation operations to be performed on input to the layer. Some neural network layers have operations that are referred to as neurons. Each neuron receives one or more inputs and generates an output that is received by another neural network layer. Often, each neuron receives inputs from other neurons, and each neuron provides an output to one or more other neurons.

An architecture of a neural network specifies what layers are included in the network and their properties, as well as how the neurons of each layer of the network are connected. In other words, the architecture specifies which layers provide their output as input to which other layers and how the output is provided.

The transformation operations of each layer are performed by computers having installed software modules that implement the transformation operations. Thus, a layer being described as performing operations means that the computers implementing the transformation operations of the layer perform the operations.

Each layer generates one or more outputs using the current values of a set of parameters for the layer. Training the neural network thus involves continually performing a forward pass on the input, computing gradient values, and updating the current values for the set of parameters for each layer using the computed gradient values. Once a neural network is trained, the final set of parameter values can be used to make predictions in a production system.

SUMMARY

This specification describes how a plant biology system can use one or more machine learning models to predict the phenotype of a plant and/or a multi-omic profile of the plant.

To generate the prediction, the machine learning models of the plant biology system can receive as input multi-omic data corresponding to the plant at one or more previous time points. The machine learning models can also receive phenotypic data characterizing the plant at the one or more previous time points. In response to the prediction of the phenotype or multi-omic profile of the plant, the plant biology system can determine to execute one or more interventions on the plant. For example, the plant biology system can deliver exogenous material to the plant, e.g., in order to modify the genome or the RNA profile of the plant. The plant biology system can also determine, using the generating prediction, one or more of: a management practice profile, an environment profile, or a breeding decision for the plant.

This specification also describes how a plant biology system can use one or more generative machine learning models to generate one or more of: a target multi-omics profile, a target management practice profile, or a target environment profile for a plant. In particular, the generative machine learning models can receive as input a desired multi-omics profile and/or a desired phenotype of the plant, and generate a model output that, if executed on the plant, causes the plant to exhibit the desired multi-omics profile and/or desired phenotype. That is, the plant biology can perform one or more interventions to modify the plant according to the generated target profiles. As a particular example, the generated target multi-omics profile can include a target genomic sequence, and the plant biology system can perform interventions to modify the genome of the plant to include the target genomic sequence.

In this specification, a "plant" can include any cell, tissue, plantlet, or full plant that belongs to the kingdom Plantae or to the kingdom Fungi. As a particular example, a system can use the techniques described in this specification to biotechnologically modify multicellular organisms belonging to the kingdom Fungi. In this specification, multi-omics data of a plant can include, but is not limited to, data characterizing any one or more of: genome, epigenome, transcriptome, proteome, metabolome, lipidome, glycome, cytome, exome, interferome, kinome, ionome, metalome, methylome, phenome, phytochemome, regulome, or secretome data, as well as "meta" data, that is, omic data of the organisms that interact with the plant, for example, meta-genome, meta-epigenome, meta-transcriptome, meta-proteome, meta-metabolome, meta-lipidome, meta-glycome, meta-cytome, meta-exome, meta-interferome, meta-kinome, meta-ionome, meta-metalome, meta-methylome, meta-phenome, meta-phytochemome, meta-regulome, or meta-secretome of the plant. In this specification, the phenotype of a plant is the set of observable characteristics or traits of the plant. In particular, in this specification, the phenotype of a plant is considered to be distinct from the multi-omics profile of the plant.

In this specification, a management practices profile of a plant can include any adjustable aspect of the management of the growth of the plant, e.g., inputs such as fertilizer or water, the timing of planting, fertilizing, harvesting, etc. In this specification, an environment profile of a plant can include the location-specific environmental conditions the plant is exposed to, e.g. temperature, precipitation, soil properties, etc.

Particular embodiments of the subject matter described in this specification can be implemented so as to realize one or more of the following advantages.

Techniques described in this specification can be used to increase the pace at which plant science experiments are performed, i.e., increase the pace of the design-build-test-learn cycle, by multiple orders of magnitude. For example, combinatorial metabolic pathways can be used to generate crops with properties that cannot be obtained using traditional breeding or even gene editing techniques. As another example, combinations of mutations arising from gene edits can also be tested at a dramatically increased rate.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes how a plant biology system can measure and model a plant state over one or more time points in its development, under one or more environmental stressor conditions during its development, and in one or more tissues so as to better understand and predict the plant's behavior and properties. Such a model can be used to significantly accelerate plant optimization.

In some implementations, the system can predict later states, including phenotypes, from earlier data. This allows the plant biology system to generate diversity within plant populations and shortcut its development times; that is, the system does not have to wait the entire lifecycle of the plant to start the next cycle of diversity generation, either through genetic modification or breeding.

In some implementations, the system can develop a generative model for plant biotechnology. For example, the system can determine one or more interventions to any one of the multi-omics categories according to the output of the generative model. As another example, the system can develop a generative model to generate target genetic sequences, target expression profiles, target environment profiles, and/or target management practice profiles for generating and growing new plants. As a particular example, the collected data can enable more successful modeling in the context of environment and management to link specific genetic variations to phenotype. A generative genetic model, wherein a specific genotype or desired range of genotypic variation can be computationally generated based on a given set of desired phenotypes or intermediate states, in the context of environments and management practices, would enable those tasked with generating genetic variation to confine that variation to a more tractable number before generating it.

Figure 1:
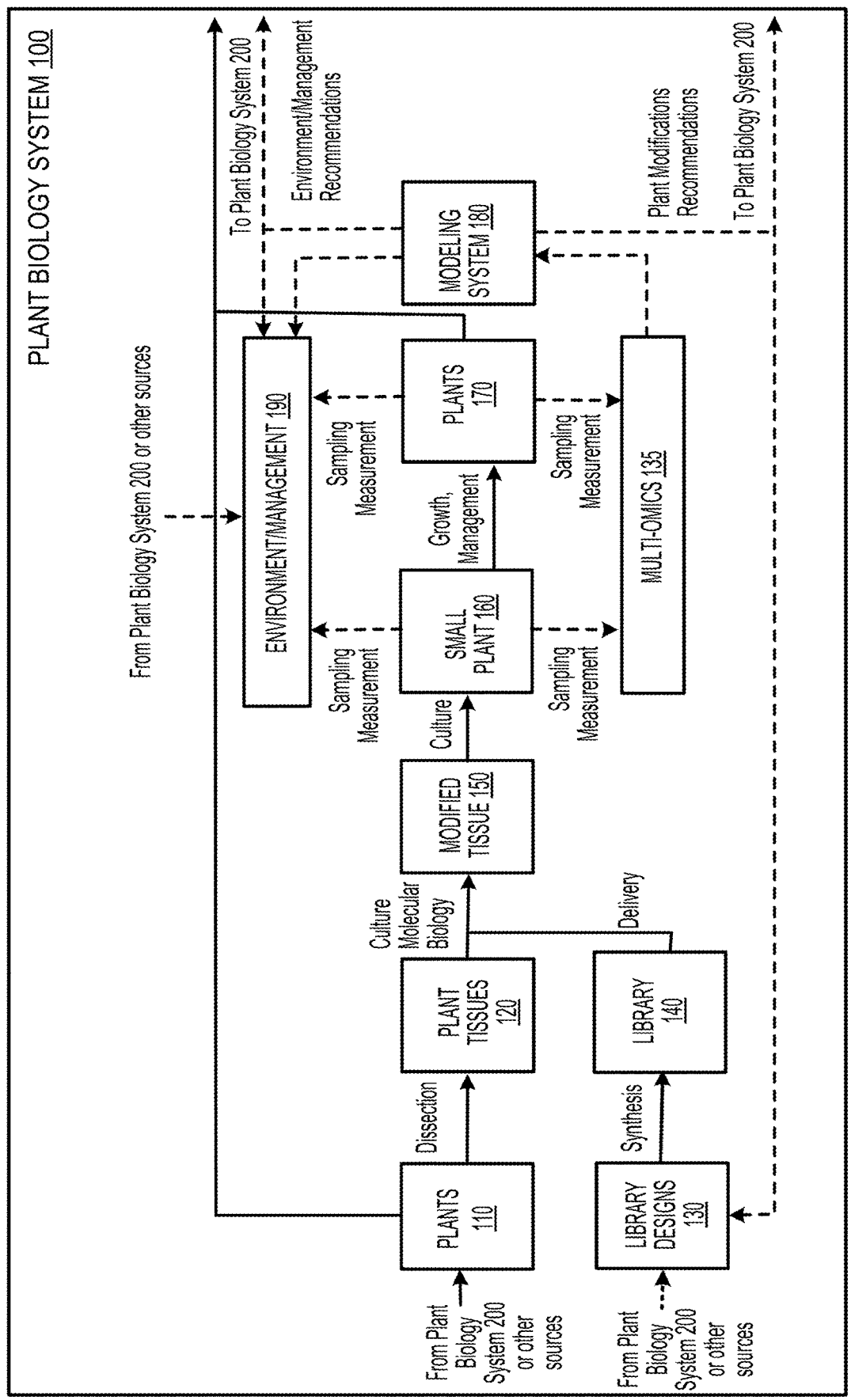
FIG. 1 is a diagram of an example plant biology system.
Figure 2:
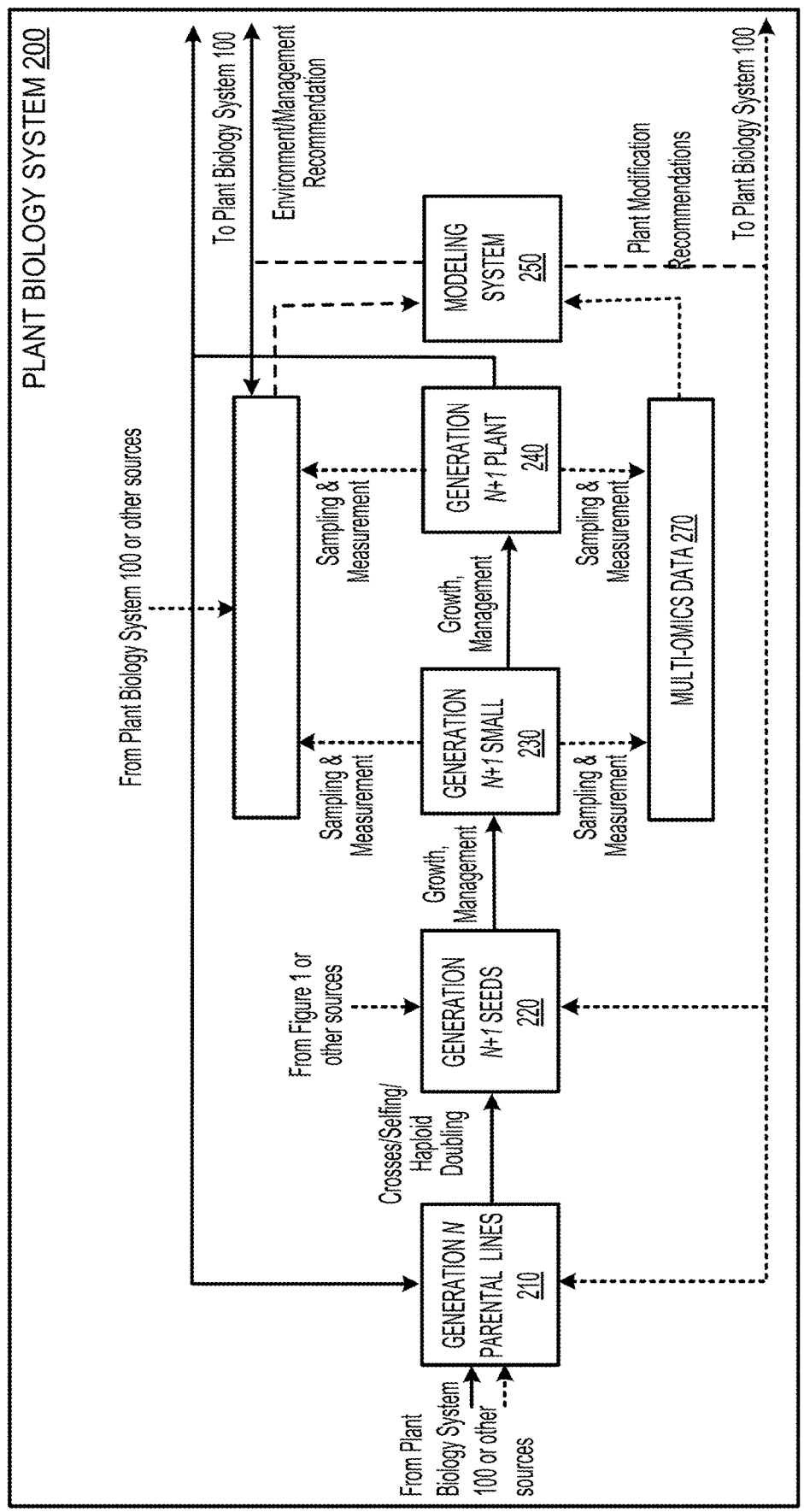
FIG. 2 is a diagram of another example plant biology system.

FIG. 1 and FIG. 2 are diagrams of example plant biology systems 100 and 200. The plant biology systems 100 and 200 are examples of systems implemented as computer programs on one or more computers in one or more locations in which the systems, components, and techniques described below are implemented.

The plant biology system 100 of FIG. 1 generates new plants using in vitro molecular biology techniques, while the plant biology system 200 of FIG. 2 generates new plants using the genetics or epigenetics of previous plants.

Generally in FIG. 1 and FIG. 2, a solid line implies the transfer of a physical object, e.g., a plant, plant tissue, or a molecule, while a dashed line indicates the transfer of data, e.g., measurement data of a plant or a model output of a machine learning model.

Referring to FIG. 1, the plant biology system 100 can execute a plant generation lifecycle by starting with a plant from a plants system 110. In some cases, the plant can be obtained from a plant system 170 in a previous lifecycle of the plant biology system 100. In some other cases, the plant can be obtained from a plant system 240 in a previous lifecycle of the plant biology system 200 depicted in FIG. 2. In some other cases, the plant can be obtained from another source such as sampling from the wild population or from conventional breeding programs. The first two cases are discussed in more detail below.

The plant can be dissected, either by an automated system, e.g., a robotic control system, or manually, and provided to a plant tissues system 120. The plant tissue can then be modified and provided to a modified tissues system 150, e.g., the plant can be genetically modified using a library 140 and a delivery method; this process is described in more detail below. A library is a collection of multiple versions of reagents, for example a collection of DNA sequences combinatorially assembled to give many different versions of a metabolic pathway. The library can, for example, include plasmids, linear DNA fragments, synthetic guide RNAs (sgRNAs), RNAs, proteins, etc. The library 140 can be generated from a library design system 130, which can be collected either from a model output generated from a model 180 in a previous lifecycle of the plant biology system 100, from a model output of a model 250 in a previous lifecycle of the plant biology system 200, or from another source, for example, manual design from experts. The first two of these cases are discussed in more detail below.

The modified tissues system 150 can grow e.g., in a culture, the modified tissues into a small plant, and provide the small plant to a small plants system 160. The small plants system 160 can be governed by an environment and management practices system 190, that dictates the environmental conditions and the management practices under which the small plants are grown. The small plants system 160 can generate samples and measurements from the small plant as it grows, extract data from the samples and measurements, and provide the extracted data to the environment and management practices system 190, which in turn provides the extracted data to the model 180, in order to determine whether the environmental and management practice profiles of the small plant are optimal.

The small plants system 160 can also provide the data extracted from the samples and measurements to a multi-omics system 195, which tracks the multi-omic profile of the small plant, in order to generate machine learning models from the data. The data extraction can include tissue sampling, molecule extraction and purification, and molecule quantification or identification to provide the multi-omics profile, and can occur in any or a multitude of separate tissues/organs of the plant. We used a dashed line here because this entire process represents the transition from a tangible entity (plant or plant tissue) to data (multi-omics). This process is discussed in more detail below.

The small plants system 160 can grow the small plant into a full plant through growth practices and environmental and management practices, and provide the grown plant to a plant system 170. The plant system 170 can also obtain samples and measurements of the full plant, extract data from the samples and measurements, and provide the data extracted from the samples and measurements to the environmental and management practice system 190 and the multi-omics system 195, as described above with reference to the small plants system 160.

The environmental and management practice system 190 and the multi-omics system 195 can provide all data gathered throughout the lifetime of the plant, i.e., every piece of multi-omics, phenotypic, environmental, and management practice data corresponding to every time point at which data was collected, to the modelling system 180. The modelling system 180 can use the data to train one or more machine learning models that the plant biology system 100 can use to guide the generation of new plants with desired qualities. The machine learning models are described in more detail below in reference to FIG. 4 and FIG. 5.

The modelling system 180 can provide the trained or updated machine learning models to i) the library designs system 130 to guide the modification of new plants, ii) the environment and management practice system 160 to guide the growth and management of small plants 160 and full plants 170, and iii) equivalent systems in the plant biology system 200. In FIG. 1 and FIG. 2, the outputs of the modeling systems are labeled as "recommendations," but generally they can be any model output of a machine learning model.

The plants system 170 can provide the fully-grown plant back to the plants system 110, in order to start a new lifecycle. The plants system 170 can also provide the fully-grown plant to the plants system 210 of the plant biology system 200 depicted in FIG. 2, in order to begin a new lifecycle of the plant biology system 200. That is, the plant biology systems 100 and 200 can provide plants and data to each other, so that a management system can use both plant biology systems 100 and 200 to iterate on plant generation.

Referring to FIG. 2, the plant biology system 200 can execute a plant generation lifecycle by starting with a generation N plant obtained from a generation N parental lines system 210. As described above, in some cases, the plant can be obtained from the generation N+1 plants system 240 in a previous lifecycle of the plant biology system 200, from the plant system 170 in a previous lifecycle of the plant biology system 100 depicted in FIG. 1, or from another source such as sampling from the wild population or from conventional breeding programs.

A generation N+1 seeds system 220 can generate new seeds from processes involving the parental lines 210, e.g., using crosses, selfing, or haploid doubling. As described above with reference to FIG. 1, a generation N+1 small plants system 230 and a generation N+1 plants system 240 can, through growth and management practices dictated by a machine learning model trained by the modelling system 250, grow the generation N+1 seeds into a fully-grown generation N+1 plant. The generation N+1 small plants system 230 and the generation N+1 plants system 240 can also obtain samples and measurements of the generation N+1 plant as it grows, and provide data extracted from the samples and measurements to an environmental and management practices system 260 and a multi-omics system 270. For example, the data extraction can include tissue sampling, molecule extraction and purification, and molecule quantification or identification to provide the multi-omics profile, and can occur in any or a multitude of separate tissues/organs of the plant.

As described above with reference to FIG. 1, the environmental and management practices system 260 and the multi-omics system 270 can provide every piece of data collected corresponding to the generation N+1 plant to the modelling system 250, which can use the data to train one or more machine learning models that the plant biology system 200 can use to guide generate new plants with desired qualities. The machine learning models are described in more detail below in reference to FIG. 4 and FIG. 5.

In some implementations, plant biology systems 100 and 200 can share the same modelings system; i.e., the modeling system 180 depicted in FIG. 1 and the modeling system 250 depicted in FIG. 2 can be the same system. Thus, both plant biology system 100 and 200 can share data to train machine learning models.

The modelling system 250 can provide the trained or updated machine learning models to i) select the next generation of parental lines for parental lines system 210 to guide the selection of plants to use for the next lifecycle, ii) develop an design for crossing, selfing, haploid doubling, or in any other way mixing the genetics of the parental lines in seeds system 220, iii) the environment and management practices system 260 to guide the growth and management of new plants, or iv) equivalent systems in the plant biology system 100.

The modeling and analysis for each time step can depend only on the current time step, or it can depend on multiple previous time steps. That is, the machine learning models of the plant biology systems can take as input either the data collected in the current time step or a time series of data collected during multiple previous time steps.

The modeling and analysis can include generating predictions for the phenotype of multi-omic profile of the new plant. Instead or in addition, the modeling and analysis can include generating a target multi-omic, management practice, or environment profile. This process is discussed in more detail below in reference to FIGS. 3-5.

One or more of the steps of the process performed by the plant biology systems 100 and/or 200 can be performed in an automated fashion. Instead or in addition, one or more of the steps can be performed in manual fashion.

As a particular example, genetic modifications can be performed by the modified tissues system 150 depicted in FIG. 1 by (a) obtaining DNA sequences from the library 140, which may be generated using a generative model, (b) performing custom DNA synthesis, and (c) performing transformation and regeneration protocols (e.g., automated transformation and regeneration protocols). This process is described in U.S. application Ser. No. 16/853,297, the entire contents of which are hereby incorporated by reference. Genetic modifications can also be generated via conventional breeding, or by gene editing, base editing, or prime editing, wherein site-specificity for site-directed DNA modifying enzymes (e.g. guide RNA designs) are the output of the generative model.

The approach described herein uses computational methods to link multi-omic and, optionally, dynamic data, with phenotypic outcomes. These methods may be species-generalizable and may include constraint-based physical models, statistical models, machine learning, and traditional biological methods. The generative modeling described herein can be accomplished by modeling the joint probability distribution of the inputs and outcomes; and modelling the conditional probability distribution of the parameters given the training data. The models described herein are enabled by increased computational power and new and flexible machine learning models. These models are discussed in more detail below in reference to FIG. 4 and FIG. 5.

This system does not suffer from the same limitations as conventional approaches. Muti-omic, time-dependent modeling is complex and computationally expensive. It is difficult to build a generic statistical model of biological systems. As a result, prior to these advances, researchers were forced to restrict the dataset (e.g., to a single-omics dataset), simplify the models (e.g., with simple linear assumptions), or otherwise constrain their approach. For this reason, it is believed that approaches that do not suffer from these restrictions would significantly improve predictive and generative performance.

Figure 3:
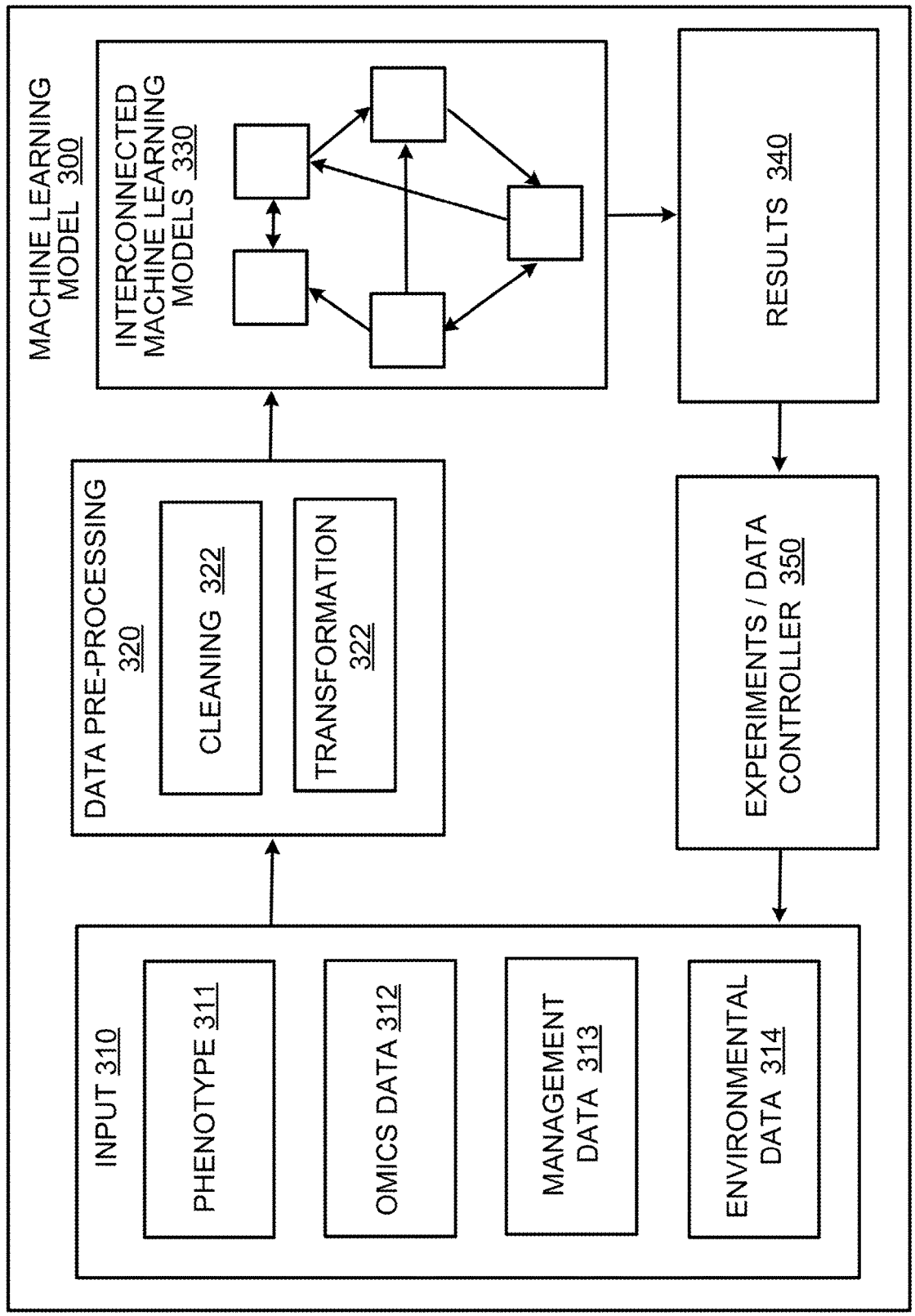
FIG. 3 is a block diagram of an example machine learning model of a plant biology system.

FIG. 3 is a block diagram of an example machine learning model 300 of a plant biology system. The machine learning model 300 is an example of a system implemented as computer programs on one or more computers in one or more locations in which the systems, components, and techniques described below are implemented.

The machine learning model 300 can receive as input data characterizing a plant at one or more previous time steps (step 310). For example, the data can include phenotypic data 311 and/or a known multi-omics profile 312 for each previous time step. The known multi-omics profile can include data characterizing any known multi-omics for the previous time step, but not necessarily every multi-omics category; that is, one or more multi-omics categories may be unknown. The input data can also include management data 313 and environment data 314 characterizing the conditions that the plant was in at the one or more previous time steps. The input data can also include genomic data, e.g., a complete or partial genomic sequence of the plant.

The machine learning model 300 can perform pre-processing on the input data to generate updated input representations, e.g., input embeddings, for the machine learning model 300. For example, the machine learning model can "clean" the input data so that the input representations match a particular template.

As another example, the machine learning models 330 can perform "dimensionality reduction." That is, one or more of the machine learning models 330 can reduce the number of inputs into one or more other machine learning models of the interconnected machine learning models 330, e.g., by processing the initial input representation provided by the inputs system 310 to generate an updated representation that is smaller than the initial representation.

The data can be stored locally or on the cloud, and downloaded or transferred to the model upon request. The pre-processing can also be performed locally or using remote servers on the cloud. Data that is created as a result of the computational process may be then saved or stored locally or on the cloud.

In this specification, an embedding is an ordered collection of numeric values that represents an input in a particular embedding space. For example, the embedding can be a vector of floating point or other numeric values that has a fixed dimensionality.

The machine learning model 300 can then process the input representation using one or more machine learning modules, or computational analysis modules, in order to generate results 340 as the modules have been trained. This process is discussed in more detail below with respect to FIG. 4 and FIG. 5.

The results 340 can then be provided to an experimental or data controller system 350 to generate more plants, as described above, and the process can cycle back to the first step at the input system 310.

Figure 4:
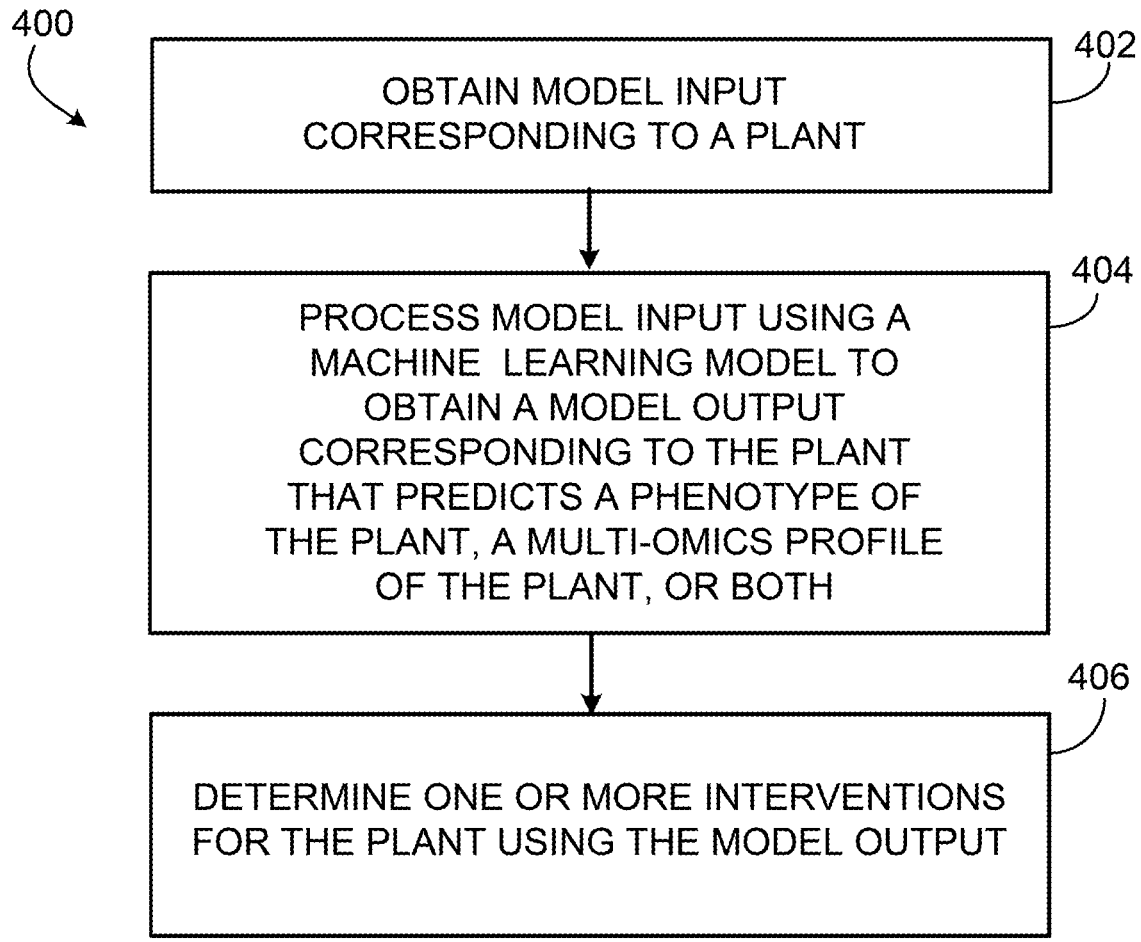
FIG. 4 is a flow diagram of an example process for predicting a phenotype and/or a multi-omics profile of a plant.
Figure 5:
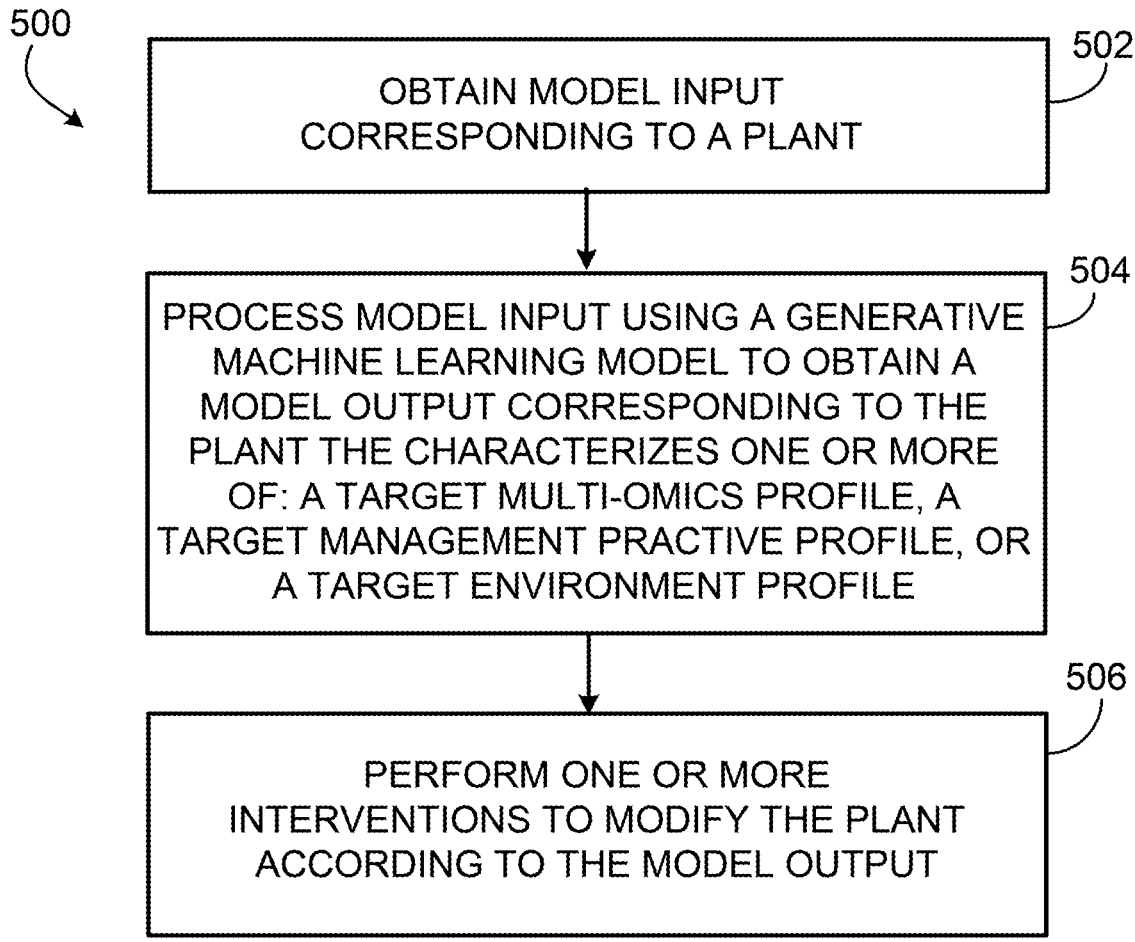
FIG. 5 is a flow diagram of an example process for generating one or more target interventions for a plant.

FIG. 4 and FIG. 5 describe example processes for using machine learning models for plant biotechnology.

In particular, FIG. 4 describes an example process for using input multi-omics data and phenotypic data of a plant to generate a prediction of output multi-omics data and phenotypic data for the plant. In some implementations, the multi-omics, phenotype, environment, and/or management categories that are used as input to the model, e.g., transcriptome, are different from the multi-omics, phenotype, environment, and/or management categories that are obtained as an output of the model, e.g., proteome. That is, the machine learning model can use data corresponding to certain multi-omics, phenotype, environment, and/or management categories at a particular time point, optionally with other data at previous time points, to generate a prediction for other multi-omics, phenotype, environment, and/or management categories at the particular time point.

In some other implementations, the number of multi-omics, phenotype, environment, and/or management categories that are used as input to the model can be different than the number multi-omics, phenotype, environment, and/or management categories that are obtained as an output of the model, e.g., the inputs can be genome and transcriptome and the output could be proteome.

In some other implementations, the multi-omics, phenotype, environment, and/or management categories that are used as input to the model can be the same as the multi-omics, phenotype, environment, and/or management categories that are obtained as an output of the model, but the input multi-omics, phenotype, environment, and/or management data corresponds to a different time point than the output multi-omics, phenotype, environment, and/or management data. That is, the machine learning model can use data corresponding to particular multi-omics, phenotype, environment, and/or management categories at previous time points to generate a prediction for the particular multi-omics, phenotype, environment, and/or management categories at the current time point, and optionally future time points.

FIG. 5, describes an example process for using input "desired" multi-omics, phenotype, environment, and/or management data to generate output "target" multi-omics, phenotype, environment, and/or management data. The target multi-omics, phenotype, environment, and/or management data, if used to perform interventions of a plant, causes the plant to exhibit the "desired" multi-omics, phenotype, environment, and/or management characteristics. Generally, the "target" multi-omics, phenotype, environment, and/or management categories and "desired" multi-omics, phenotype, environment, and/or management categories are different.

Generally, a multi-omics, phenotype, environment, and/or management category that is used as an input to the process described in FIG. 4 (e.g., a multi-omics category that can be used to predict the phenotype or other multi-omics categories in a plant) can be used as an output to the process described in FIG. 5 (e.g., a "target" multi-omics category that can be used to effectuate a desired phenotype or other multi-omics categories in the plant).

FIG. 4 is a flow diagram of an example process 400 for predicting a phenotype and/or a multi-omics profile of a plant. For convenience, the process 400 will be described as being performed by a system of one or more computers located in one or more locations. For example, a plant biology system, e.g., the plant biology system 100 depicted in FIG. 1, appropriately programmed in accordance with this specification, can perform the process 400.

The system obtains a model input corresponding to the plant (step 402). The model input can include time series data that includes data for one or more previous time points. The data for each previous time point can include i) a multi-omics profile of the plant at the previous time points, ii) phenotypic data corresponding to the plant at the previous time point, or iii) both. The data for each previous time point can also include the management practice profile and/or the environment profile of the plant at the previous time point; that is, the data for each previous time point can include data characterizing the conditions in which the plant grew at the previous time point.

The system processes the model input using a machine learning model to obtain a model output corresponding to the plant at one or more future time points (step 404). The model output can include, for each future time point of the one or more future time points, that a prediction for i) the phenotype of the plant at the future time point, ii) a multi-omics profile of the plant at the future time point, or iii) both. The machine learning model can be configured through training to receive such model inputs to generate such model outputs.

In some implementations, the final "previous" time step in the model input is the same time step as the first "future" time step in the model output, i.e., a "current" time point.

In some implementations, the machine learning model includes a hybrid model, where the hybrid model comprises i) a machine learning component and ii) a hard-coded component. As a particular example, the hard-coded component can include one or more look-up tables, e.g., a look-up table that maps genetic sequences to proteins, a lookup table related to protein folding, a lookup table that defines regulatory sequences, a lookup table that maps regulatory sequence to expression level, a lookup table that maps protein sequence or identity to enzymatic function, a lookup table that maps protein sequence or identity to enzyme kinetics, or a lookup table that gives annealing temperatures of polymers.

The system determines one or more interventions for the plant using the model output (step 406). For example, the system can determine a management practice profile for the plant using the model output, e.g., by selecting one or more management practices for the plant according to the model output. As another example, the system can determine an environment profile of the plant using the model output, e.g., by selecting a value for each of one or more environment variables according to the model output. As another example, the system can determine a breeding decision for the plant using the model output. As another example, the system can determine, according to the model output, to deliver exogenous material to the plant, e.g., by performing one or more of: modifying the genome of the plant, editing the RNA of the plant, modulating the levels of certain transcripts within the plant, or delivering proteins to the plant. Modifications can be made in such a way as to be effective at a particular time or times, or a specific tissue or tissue, for example by modifying the regulatory elements controlling gene expression.

FIG. 5 is a flow diagram of an example process 500 for generating one or more target interventions for a plant. For convenience, the process 500 will be described as being performed by a system of one or more computers located in one or more locations. For example, a plant biology system, e.g., the plant biology system 100 depicted in FIG. 1, appropriately programmed in accordance with this specification, can perform the process 500.

The system obtains a model input corresponding to the plant (step 502). The model input can include time series data that includes data for one or more previous time points. The data for each previous time point can include i) a multi-omics profile of the plant at the previous time point, ii) phenotypic data corresponding to the plant at the previous time point, or iii) both. The data for each previous time point can also include the management practice profile and/or the environment profile of the plant at the previous time point; that is, the data for each previous time point can include data characterizing the conditions in which the plant grew at the previous time point.

The system processes the model input using a generative machine learning model to obtain a model output corresponding to the plant that characterizes one or more of: a target multi-omics profile, a target management practice profile, or a target environment profile (step 504).

The generative machine learning model can be configured through training to receive a model input that identifies desired qualities of a plant, and process the model input to generate one or more of i) a target multi-omics profile, ii) a target management practice profile, or iii) a target environment profile that, when used to modify the plant, causes the plant to exhibit the desired qualities. That is, the model output accomplishes the desired goals characterized by the model input.

The generative machine learning model can include one or more of: a generative adversarial network; a probabilistic deep learning model; a Bayesian model; a probabilistic kernel method; a stochastic method; a sequence prediction model; an energy-based model; one or more density estimation models in combination with one or more predictive model(s); or a combination probabilistic-non-probabilistic model.

The system performs one or more interventions to modify the plant according to the model output (step 506).

As a particular example, model output can include a target genomic sequence, and the system can perform one or more interventions to modify the genome of the plant to include the target genomic sequence. For example, the system can deliver nucleic acids and proteins to the plant, for example by using bacterial delivery, viral delivery, chemical delivery, biolistics, nanoparticle delivery, or microinjection. These delivered reagents can be used to modify the genome, for example to perform gene editing or base editing. As another particular example, the interventions can include the incorporation of genetic diversity from other plants of the same species, for example by breeding, selfing, or the use of doubled-haploid technology. This process is discussed in more detail in "*Doubled Haploid Production in Crop Plants: A Manual*," edited by Maluszynski et al., DOI: 10.1007/978-94-017-1293-4_46.

Figure 6:
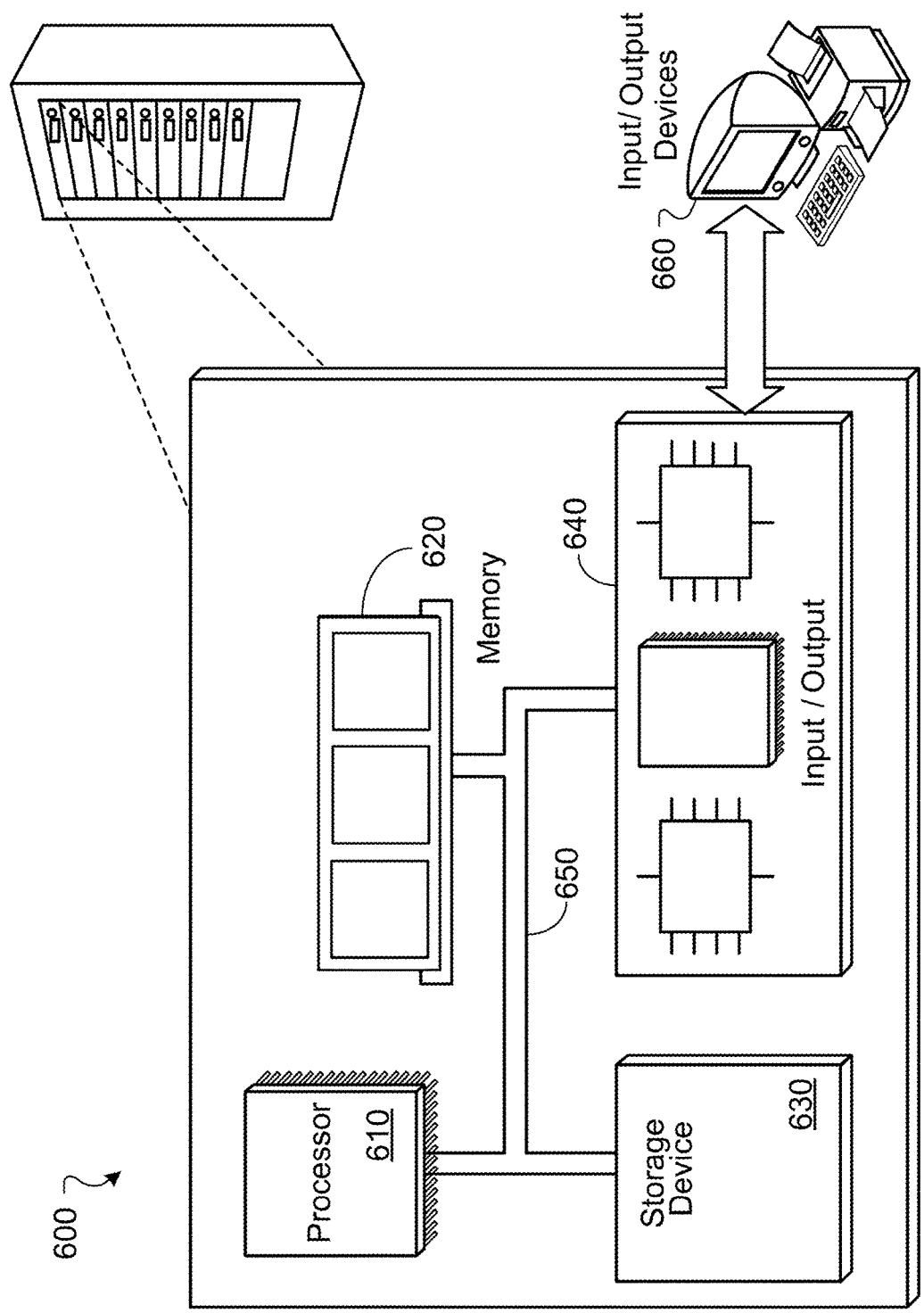
FIG. 6 is a block diagram of an example computer system.

FIG. 6 is a block diagram of an example computer system 600 that can be used to perform operations described above. The system 600 includes a processor 610, a memory 620, a storage device 630, and an input/output device 640. Each of the components 610, 620, 630, and 640 can be interconnected, for example, using a system bus 650. The processor 610 is capable of processing instructions for execution within the system 600. In one implementation, the processor 610 is a single-threaded processor. In another implementation, the processor 610 is a multi-threaded processor. The processor 610 is capable of processing instructions stored in the memory 620 or on the storage device 630.

The memory 620 stores information within the system 600. In one implementation, the memory 620 is a computer-readable medium. In one implementation, the memory 620 is a volatile memory unit. In another implementation, the memory 620 is a non-volatile memory unit.

The storage device 630 is capable of providing mass storage for the system 600. In one implementation, the storage device 630 is a computer-readable medium. In various different implementations, the storage device 630 can include, for example, a hard disk device, an optical disk device, a storage device that is shared over a network by multiple computing devices (for example, a cloud storage device), or some other large capacity storage device.

The input/output device 640 provides input/output operations for the system 600. In one implementation, the input/output device 640 can include one or more network interface devices, for example, an Ethernet card, a serial communication device, for example, a RS-232 port, and/or a wireless interface device, for example, a 802.11 card. In another implementation, the input/output device can include driver devices configured to receive input data and send output data to other input/output devices, for example, keyboard, printer and display devices 660. Other implementations, however, can also be used, such as mobile computing devices, mobile communication devices, set-top box television client devices, etc.

Although an example processing system has been described in FIG. 6, implementations of the subject matter and the functional operations described in this specification can be implemented in other types of digital electronic circuitry, or in computer software, firmware, or hardware, including the structures disclosed in this specification and their structural equivalents, or in combinations of one or more of them.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, off-the-shelf or custom-made parallel processing subsystems, e.g., a GPU or another kind of special-purpose processing subsystem. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program which may also be referred to or described as a program, software, a software application, an app, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and pointing device, e.g, a mouse, trackball, or a presence sensitive display or other surface by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network.

Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

In addition to the embodiments described above, the following embodiments are also innovative:

Embodiment 1 is a method comprising:
  obtaining a model input comprising time series data, wherein the time series data comprises, for each previous time point of one or more previous time points, at least one of i) first multi-omics data corresponding to a plant at the previous time point, or ii) phenotypic data corresponding to the plant at the previous time point; and
  processing the model input using a machine learning model to obtain a model output that comprises, for each future time point of one or more of future time points, a prediction of at least one of i) a phenotype of the plant at the future time point, or ii) second multi-omics data corresponding to the plant at the future time point, wherein the machine learning model has been configured through training to:
    receive a training model input corresponding to a training plant, and
    process the training model input to generate a prediction corresponding to the training plant at each of one or more future time points.

Embodiment 2 is the method of embodiment 1, further comprising determining, according to the model output, to deliver exogenous material to the plant, comprising one or more of:
  modifying the genome of the plant;
  editing the RNA of the plant;
  modifying the levels of particular transcripts in the plant, or delivering proteins to the plant.

Embodiment 3 is the method of any one of embodiments 1 or 2, further comprising one or more of:
  determining a management practice profile of the plant using the model output;
  determining an environment profile of the plant using the model output; or
  determining a breeding decision for the plant using the model output.

Embodiment 4 is the method of any one of embodiments 1-3, wherein the time series data further comprises, for each previous time point of the one or more previous time points, one or more of environment or management practice data.

Embodiment 5 is the method of any one of embodiments 1-4, wherein each of the first multi-omics data and the second multi-omics data comprises one or more of: genome, epigenome, transcriptome, proteome, metabolome, lipidome, glycome, cytome, exome, interferome, kinome, ionome, metalome, methylome, phenome, phytochemome, regulome, secretome data, meta-genome, meta-epigenome, meta-transcriptome, meta-proteome, meta-metabolome, meta-lipidome, meta-glycome, meta-cytome, meta-exome, meta-interferome, meta-kinome, meta-ionome, meta-metalome, meta-methylome, meta-phenome, meta-phytochemome, meta-regulome, or meta-secretome data.

Embodiment 6 is the method of any one of embodiments 1-5, wherein the machine learning model is a hybrid model, wherein the hybrid model comprises i) a machine-learned component and ii) an encoded component.

Embodiment 7 is a method comprising:
obtaining a model input comprising at least one of i) a desired multi-omics profile of a plant, or ii) a desired phenotype of the plant;
processing the model input using a generative machine learning model to obtain a model output comprising one or more of:
  a target multi-omics profile,
  a target management practice profile, or
  a target environment profile,
wherein the generative machine learning model has been configured through training to:
  receive a training model input that identifies desired qualities of a training plant, and
  process the training model input to generate one or more of i) a target multi-omics profile, ii) a target management practice profile, or iii) a target environment profile that, when used to modify the training plant, causes the training plant to exhibit the desired qualities; and
performing one or more interventions to modify the plant according to the model output.

Embodiment 8 is the method of embodiment 7, wherein:
the model input comprises a target multi-omics profile,
the target multi-omics profile comprises a target genomic sequence, and
performing one or more interventions to modify the plant comprises modifying the genome of the plant to include the target genomic sequence.

Embodiment 9 is the method of embodiment 8, wherein:
the modification is in a regulatory region, and
is directed toward one or more specific tissues of the plant, one or more developmental stages of the plant, and/or one or more environmental conditions that the plant is in.

Embodiment 10 is the method of any one of embodiments 8 or 9, wherein modifying the genome of the plant comprises one or more of:
  delivering nucleic acids and proteins to the plant; and
  performing gene editing or base editing.

Embodiment 11 is the method of any one of embodiments 7-10, wherein the target multi-omics profile comprises one or more of: genome, epigenome, transcriptome, proteome, metabolome, lipidome, glycome, cytome, exome, interferome, kinome, ionome, metalome, methylome, phenome, phytochemome, regulome, secretome data, meta-genome, meta-epigenome, meta-transcriptome, meta-proteome, meta-metabolome, meta-lipidome, meta-glycome, meta-cytome, meta-exome, meta-interferome, meta-kinome, meta-ionome, meta-metalome, meta-methylome, meta-phenome, meta-phytochemome, meta-regulome, or meta-secretome data.

Embodiment 12 is the method of any one of embodiments 7-11, wherein the one or more interventions comprise one or more of:
  breeding;
  bacterial delivery;
  viral delivery;
  chemical delivery;
  biolistics;
  nanoparticle delivery; or microinjection.

Embodiment 13 is the method of any one of embodiments 7-12, wherein the generative machine learning model comprises one or more of:
  a generative adversarial network;
  a probabilistic deep learning model;
  a Bayesian model;
  a probabilistic kernel method;
  a stochastic method;
  a sequence prediction model;
  an energy-based model;
  one or more density estimation models in combination with one or more predictive model(s); or a combination probabilistic-non-probabilistic model.

Embodiment 14 is a system comprising: one or more computers and one or more storage devices storing instructions that are operable, when executed by the one or more computers, to cause the one or more computers to perform the method of any one of embodiments 1 to 13.

Embodiment 15 is a computer storage medium encoded with a computer program, the program comprising instructions that are operable, when executed by data processing apparatus, to cause the data processing apparatus to perform the method of any one of embodiments 1 to 13.

EXAMPLES

Example 1—Experimental Evidence

Figure 7:
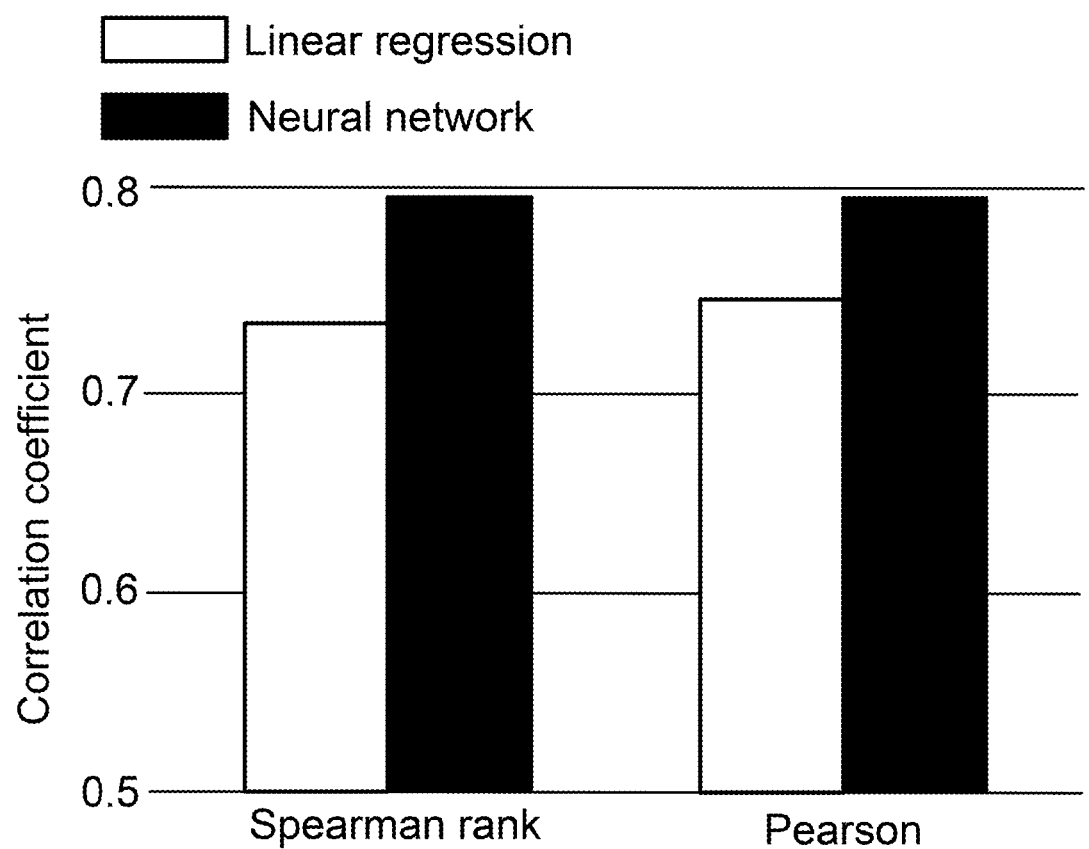
FIG. 7 is a graph showing a comparison of model performance to baseline on the same hold-out dataset.

A sequential neural network was built to model the time taken by natural genetic variant lines of *Arabidopsis thaliana* to reach the reproductive stage (time to flower). In one example, the model was trained on publicly available transcriptomes collected from leaves (Kawakatsu et al., 2016, Cell, 166(2):492-505). The transcriptomic data was available for 728 natural genetic variants, 620 of which carried flowering time information (in days to bud initiation from planting). The transcriptomic data was experimentally generated by RNA-sequencing, and the raw data was subsequently preprocessed in accordance with best practices. This step includes standardizing the original 24, 175 transcript counts (features) to unit variance, and reducing the dimensionality of the feature set by principal component analysis to the maximal allowable components—that is 558 plant lines for the given dataset (90% of all lines). In accordance with machine learning best practices, a hold-out dataset was created prior to model training, which contained 10% of the original data. The remaining 90% of the data was used to train the models. These included (1) a linear regression model as a baseline comparison, and (2) a multitude of sequential neural networks architectures as searched for by the algorithm in the AutoKeras implementation (Jin et al., 2019, In Proceedings of the 25th ACM SIGKDD International Conference on Knowledge Discovery & Data Mining (pp. 1946-1956)). The highest performing neural network model architecture-measured as the lowest mean-squared-error on a 10% validation dataset-obtained following the neural network architecture search using AutoKeras was subsequently cross-validated on the full dataset. Pearson correlation and Spearman rank correlation coefficients were used to assess and compare model performance to baseline on the same hold-out dataset (FIG. 7).

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method comprising:
   obtaining a model input comprising at least one of i) a desired multi-omics profile of a plant, or ii) a desired phenotype of the plant;
   processing the model input using a generative machine learning model to obtain a model output comprising one or more of:
   a target multi-omics profile,
   a target management practice profile, or
   a target environment profile,
   wherein the generative machine learning model has been configured through training to:
   receive a training model input that identifies desired qualities of a training plant, and
   process the training model input to generate one or more of i) a target multi-omics profile, ii) a target management practice profile, or iii) a target environment profile that, when used to modify the training plant, causes the training plant to exhibit the desired qualities; and
   determining that one or more interventions should be performed to modify the plant according to the model output.

2. The method of claim 1, wherein:
   the model input comprises a target multi-omics profile,
   the target multi-omics profile comprises a target genomic sequence, and
   performing one or more interventions to modify the plant comprises modifying the genome of the plant to include the target genomic sequence.

3. The method of claim 2, wherein:
   the modification is in a regulatory region, and is directed toward one or more specific tissues of the plant, one or more developmental stages of the plant, and/or one or more environmental conditions that the plant is in.

4. The method of claim 2, wherein modifying the genome of the plant comprises one or more of:
   delivering nucleic acids and proteins to the plant; and
   performing gene editing or base editing.

5. The method of claim 1, wherein the target multi-omics profile comprises one or more of:
   genome, epigenome, transcriptome, proteome, metabolome, lipidome, glycome, cytome, exome, interferome, kinome, ionome, metalome, methylome, phenome, phytochemome, regulome, secretome data, meta-genome, meta-epigenome, meta-transcriptome, meta-proteome, meta-metabolome, meta-lipidome, meta-glycome, meta-cytome, meta-exome, meta-interferome, meta-kinome, meta-ionome, meta-metalome, meta-methylome, meta-phenome, meta-phytochemome, meta-regulome, or meta-secretome data.

6. The method of claim 1, wherein the one or more interventions comprise one or more of:
   breeding;
   bacterial delivery;
   viral delivery;
   chemical delivery;
   biolistics;
   nanoparticle delivery; or
   microinjection.

7. The method of claim 1, wherein the generative machine learning model comprises one or more of:
   a generative adversarial network;
   a probabilistic deep learning model;
   a Bayesian model;
   a probabilistic kernel method;
   a stochastic method;
   a sequence prediction model;
   an energy-based model;
   one or more density estimation models in combination with one or more predictive model(s); or
   a combination probabilistic-non-probabilistic model.

8. A system comprising:
   one or more computers; and
   one or more storage devices communicatively coupled to the one or more computers, wherein the one or more storage devices store instructions that, when executed by the one or more computers, cause the one or more computers to perform operations comprising:
   obtaining a model input comprising at least one of i) a desired multi-omics profile of a plant, or ii) a desired phenotype of the plant;
   processing the model input using a generative machine learning model to obtain a model output comprising one or more of:
   a target multi-omics profile,
   a target management practice profile, or
   a target environment profile,
   wherein the generative machine learning model has been configured through training to:
   receive a training model input that identifies desired qualities of a training plant, and
   process the training model input to generate one or more of i) a target multi-omics profile, ii) a target management practice profile, or iii) a target environment profile that, when used to modify the training plant, causes the training plant to exhibit the desired qualities; and determining that one or more interventions should be performed to modify the plant according to the model output.

9. The system of claim 8, wherein:
the model input comprises a target multi-omics profile,
the target multi-omics profile comprises a target genomic sequence, and
performing one or more interventions to modify the plant comprises modifying the genome of the plant to include the target genomic sequence.

10. The system of claim 9, wherein:
the modification is in a regulatory region, and
is directed toward one or more specific tissues of the plant, one or more developmental stages of the plant, and/or one or more environmental conditions that the plant is in.

11. The system of claim 9, wherein modifying the genome of the plant comprises one or more of:
delivering nucleic acids and proteins to the plant; and
performing gene editing or base editing.

12. The system of claim 8, wherein the target multi-omics profile comprises one or more of:
genome, epigenome, transcriptome, proteome, metabolome, lipidome, glycome, cytome, exome, interferome, kinome, ionome, metalome, methylome, phenome, phytochemome, regulome, secretome data, meta-genome, meta-epigenome, meta-transcriptome, meta-proteome, meta-metabolome, meta-lipidome, meta-glycome, meta-cytome, meta-exome, meta-interferome, meta-kinome, meta-ionome, meta-metalome, meta-methylome, meta-phenome, meta-phytochemome, meta-regulome, or meta-secretome data.

13. The system of claim 8, wherein the one or more interventions comprise one or more of:
breeding;
bacterial delivery;
viral delivery;
chemical delivery;
biolistics;
nanoparticle delivery; or
microinjection.

14. The system of claim 8, wherein the generative machine learning model comprises one or more of:
a generative adversarial network;
a probabilistic deep learning model;
a Bayesian model;
a probabilistic kernel method;
a stochastic method;
a sequence prediction model;
an energy-based model;
one or more density estimation models in combination with one or more predictive model(s); or
a combination probabilistic-non-probabilistic model.

15. One or more non-transitory computer storage media storing instructions that when executed by one or more computers cause the one or more computers to perform operations comprising:
obtaining a model input comprising at least one of i) a desired multi-omics profile of a plant, or ii) a desired phenotype of the plant;
processing the model input using a generative machine learning model to obtain a model output comprising one or more of:
a target multi-omics profile,
a target management practice profile, or
a target environment profile,
wherein the generative machine learning model has been configured through training to:
receive a training model input that identifies desired qualities of a training plant, and
process the training model input to generate one or more of i) a target multi-omics profile, ii) a target management practice profile, or iii) a target environment profile that, when used to modify the training plant, causes the training plant to exhibit the desired qualities; and
determining that one or more interventions should be performed to modify the plant according to the model output.

16. The non-transitory computer storage media of claim 15, wherein:
the model input comprises a target multi-omics profile,
the target multi-omics profile comprises a target genomic sequence, and
performing one or more interventions to modify the plant comprises modifying the genome of the plant to include the target genomic sequence.

17. The non-transitory computer storage media of claim 16, wherein:
the modification is in a regulatory region, and
is directed toward one or more specific tissues of the plant, one or more developmental stages of the plant, and/or one or more environmental conditions that the plant is in.

18. The non-transitory computer storage media of claim 16, wherein modifying the genome of the plant comprises one or more of:
delivering nucleic acids and proteins to the plant; and
performing gene editing or base editing.

19. The non-transitory computer storage media of claim 15, wherein the target multi-omics profile comprises one or more of: genome, epigenome, transcriptome, proteome, metabolome, lipidome, glycome, cytome, exome, interferome, kinome, ionome, metalome, methylome, phenome, phytochemome, regulome, secretome data, meta-genome, meta-epigenome, meta-transcriptome, meta-proteome, meta-metabolome, meta-lipidome, meta-glycome, meta-cytome, meta-exome, meta-interferome, meta-kinome, meta-ionome, meta-metalome, meta-methylome, meta-phenome, meta-phytochemome, meta-regulome, or meta-secretome data.

20. The non-transitory computer storage media of claim 15, wherein the one or more interventions comprise one or more of:
breeding;
bacterial delivery;
viral delivery;
chemical delivery;
biolistics;
nanoparticle delivery; or
microinjection.

* * * * *